(12) United States Patent
Bonutti et al.

(10) Patent No.: US 12,138,191 B2
(45) Date of Patent: Nov. 12, 2024

(54) ORTHOSIS FOR RANGE OF MOTION

(71) Applicant: BONUTTI RESEARCH, INC., Effingham, IL (US)

(72) Inventors: Boris Bonutti, Effingham, IL (US); Glen A. Phillips, Effingham, IL (US); Peter M. Bonutti, Manalapan, FL (US); Ricke Shamhart, Wheeler, IL (US); Joseph Mathewson, Effingham (IL)

(73) Assignee: BONUTTI RESEARCH, INC., Effingham, IL (US)

( * ) Notice: Subject to any disclaimer, the term of this patent is extended or adjusted under 35 U.S.C. 154(b) by 813 days.

(21) Appl. No.: 15/350,656

(22) Filed: Nov. 14, 2016

(65) Prior Publication Data
US 2017/0135841 A1     May 18, 2017

Related U.S. Application Data

(60) Provisional application No. 62/255,023, filed on Nov. 13, 2015.

(51) Int. Cl.
| | | |
|---|---|---|
| A61F 5/00 | (2006.01) | |
| A61F 5/01 | (2006.01) | |
| A61F 5/042 | (2006.01) | |

(52) U.S. Cl.
CPC ............ *A61F 5/0127* (2013.01); *A61F 5/042* (2013.01); *A61F 2005/0153* (2013.01); *A61F 2005/0158* (2013.01); *A61F 2005/0179* (2013.01)

(58) Field of Classification Search
CPC .... A61F 5/0195; A61F 5/0111; A61F 5/0127; A61F 5/00; A61F 5/01; A61F 5/0102; A61F 5/0104; A61F 5/0113; A61F 5/0116; A61F 5/058; A61F 5/0585; A61F 2005/0132; A61F 2005/0137; A61F 2005/0139; A61F 2005/0146; A61F 2005/011; A61F 2005/0153; A61F 2005/0155; A61F 2005/0179; A61F 2005/0197; A61F 5/013; A61F 5/04; A61F 5/042; A61F 5/048; A61F 2005/0134
USPC .............................................. 602/26, 27, 28
See application file for complete search history.

(56) References Cited

U.S. PATENT DOCUMENTS

| | | | | |
|---|---|---|---|---|
| 5,036,837 A | * | 8/1991 | Mitchell ............... | A61F 5/0123 602/16 |
| 5,102,411 A | | 4/1992 | Hotchkiss et al. | |
| 5,437,611 A | | 8/1995 | Stern | |
| 5,472,410 A | * | 12/1995 | Hamersly ............ | A61F 5/0125 601/33 |
| 5,571,078 A | * | 11/1996 | Malewicz ............ | A61F 5/0125 128/882 |
| 5,575,764 A | | 11/1996 | Van Dyne | |
| 6,001,075 A | | 12/1999 | Clemens et al. | |
| 7,473,234 B1 | | 1/2009 | Weltner et al. | |
| 7,517,330 B2 | | 4/2009 | Deharde et al. | |
| 8,206,329 B2 | | 6/2012 | Bonutti et al. | |

(Continued)

*Primary Examiner* — Adam Baker
(74) *Attorney, Agent, or Firm* — Stinson LLP

(57) ABSTRACT

An ankle stretch orthosis includes a foot assembly having a ball support assembly adjustably mounted on a foot plate. The foot assembly includes an adjustment mechanism for selectively adjusting a position of ball support assembly relative to the foot plate to align the ball support assembly with a ball portion of a foot that is one of supinated and pronated.

12 Claims, 18 Drawing Sheets

(56) References Cited

U.S. PATENT DOCUMENTS

| | | | | |
|---|---|---|---|---|
| 8,257,283 | B2* | 9/2012 | Kaiser | A61H 1/0285 601/5 |
| 2004/0267176 | A1* | 12/2004 | Houser | A61F 5/0123 602/16 |
| 2007/0219475 | A1* | 9/2007 | Bonutti | A61F 5/0127 602/16 |
| 2014/0068838 | A1* | 3/2014 | Beers | A61F 5/028 2/243.1 |
| 2016/0173665 | A1* | 6/2016 | Hantsch | F16H 57/021 455/575.1 |

* cited by examiner

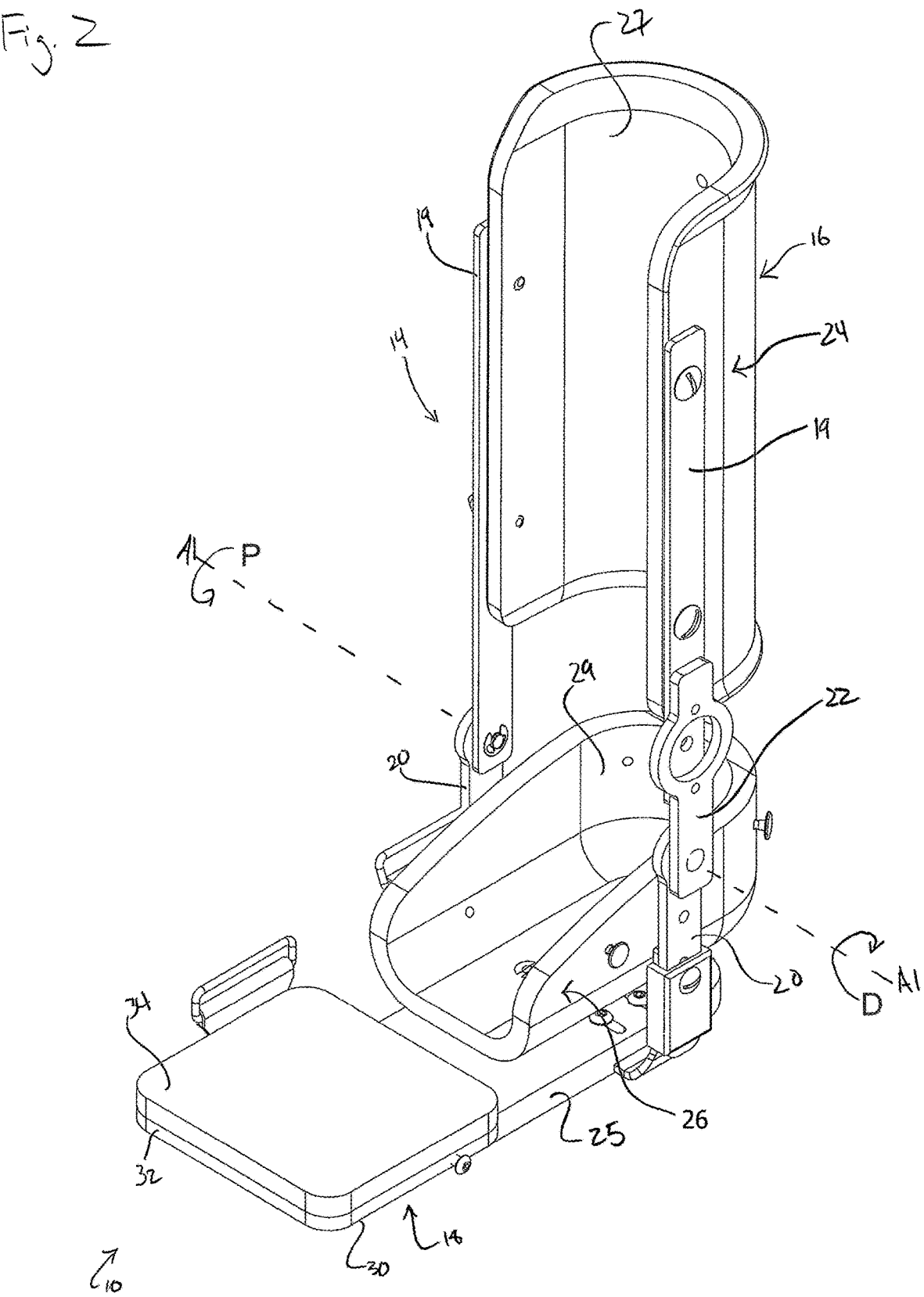

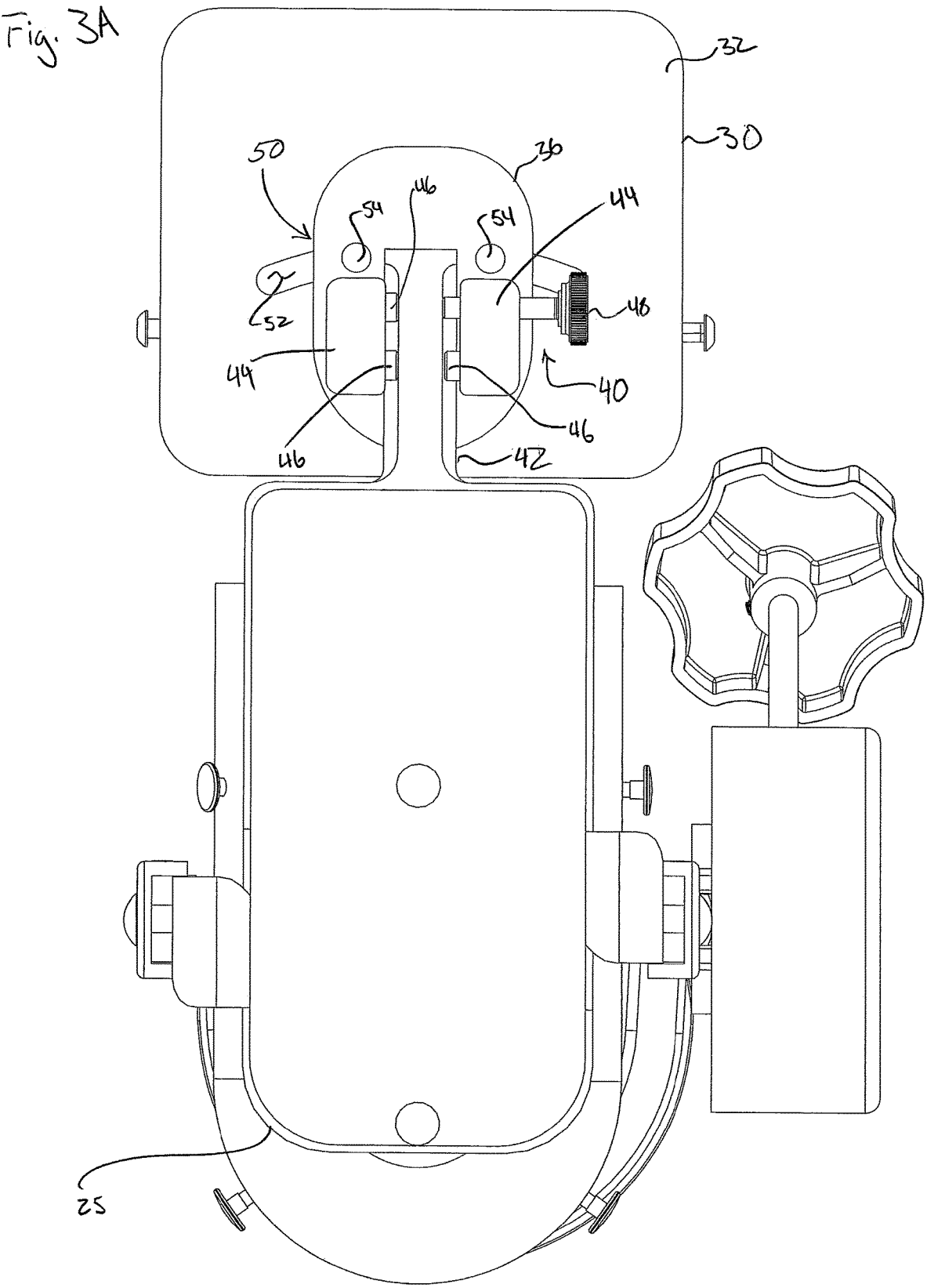

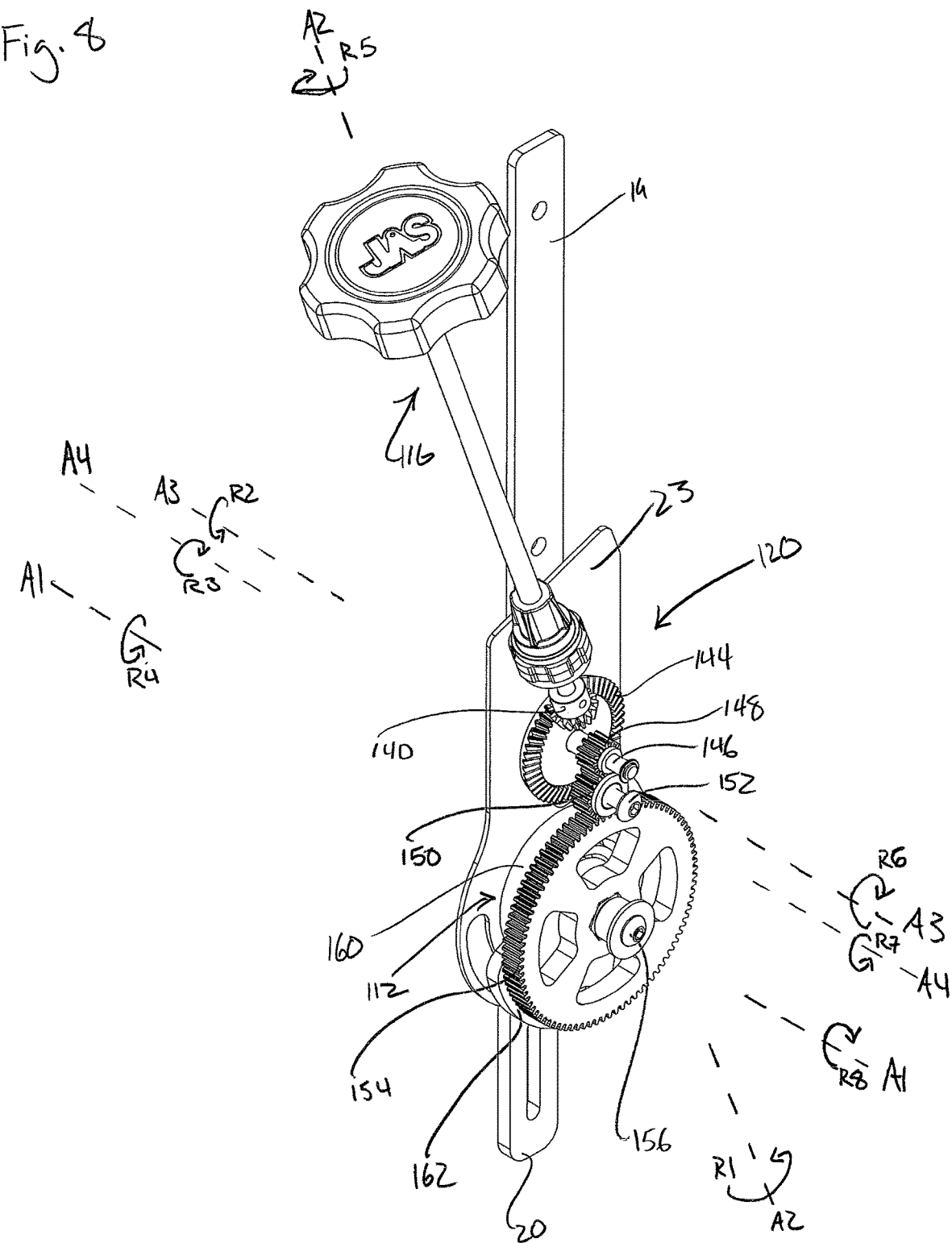

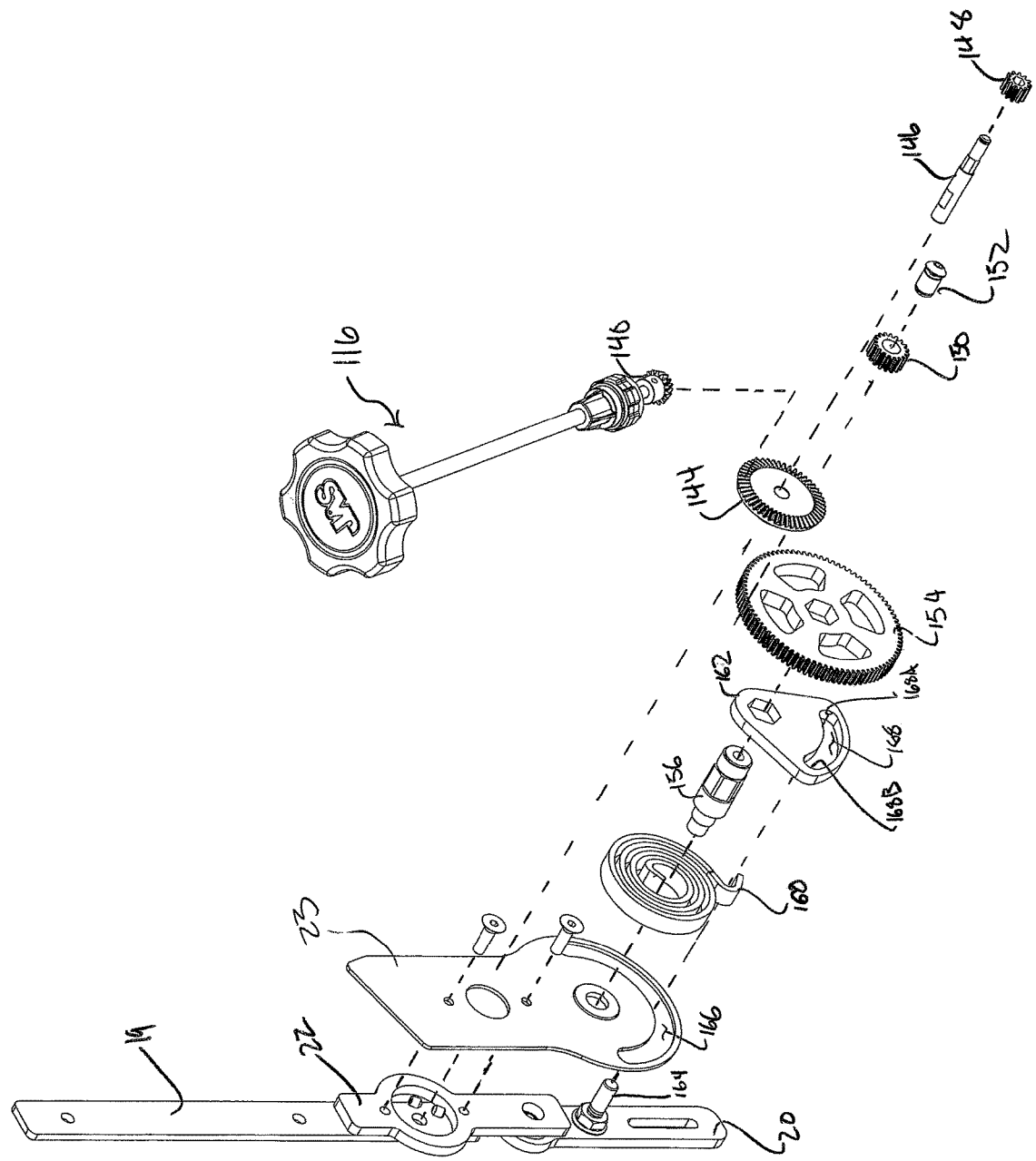

ORTHOSIS FOR RANGE OF MOTION

CROSS-REFERENCE TO RELATED APPLICATIONS

The present application claims priority to U.S. Provisional Application No. 62/255,023, filed Nov. 13, 2015, the entirety of which is hereby incorporated by reference.

FIELD OF THE DISCLOSURE

The present disclosure generally relates to an orthosis for treating a joint of a subject, and in particular, an orthosis for increasing range of motion of the joint of the subject.

BACKGROUND OF THE DISCLOSURE

In a joint of a body, its range of motion depends upon the anatomy and condition of that joint and on the particular genetics of each individual. Many joints primarily move either in flexion or extension, although some joints also are capable of rotational movement in varying degrees. Flexion is to bend the joint and extension is to straighten the joint; however, in the orthopedic convention some joints only flex. Some joints, such as the knee, may exhibit a slight internal or external rotation during flexion or extension. Other joints, such as the elbow or shoulder, not only flex and extend but also exhibit more rotational range of motion, which allows them to move in multiple planes. The elbow joint, for instance, is capable of supination and pronation, which is rotation of the hand about the longitudinal axis of the forearm placing the palm up or the palm down. Likewise, the shoulder is capable of a combination of movements, such as abduction, internal rotation, external rotation, flexion and extension.

When a joint is injured, either by trauma or by surgery, scar tissue can form or tissue can contract and consequently limit the range of motion of the joint. For example, adhesions can form between tissues and the muscle can contract itself with permanent muscle contracture or tissue hypertrophy such as capsular tissue or skin tissue. Lost range of motion may also result from trauma such as excessive temperature (e.g., thermal or chemical burns) or surgical trauma so that tissue planes which normally glide across each other may become adhered together to markedly restrict motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis.

ROM orthoses are used during physical rehabilitative therapy to increase the range-of-motion of a body joint. Additionally, they also may be used for tissue transport, bone lengthening, stretching of skin or other tissue, tissue fascia, and the like. When used to treat a joint, the device typically is attached on body portions on opposite sides of the joint so that is can apply a force to move the joint in opposition to the contraction.

A number of different configurations and protocols may be used to increase the range of motion of a joint. For example, stress relaxation techniques may be used to apply variable forces to the joint or tissue while in a constant position. "Stress relaxation" is the reduction of forces, over time, in a material that is stretched and held at a constant length. Relaxation occurs because of the realignment of fibers and elongation of the material when the tissue is held at a fixed position over time. Treatment methods that use stress relaxation are serial casting and static splinting. One example of devices utilizing stress relaxation is the JAS EZ orthosis, Joint Active Systems, Inc., Effingham, IL.

Sequential application of stress relaxation techniques, also known as Static Progressive Stretch ("SPS") uses the biomechanical principles of stress relaxation to restore range of motion (ROM) in joint contractures. SPS is the incremental application of stress relaxation—stretch to position to allow tissue forces to drop as tissues stretch, and then stretching the tissue further by moving the device to a new position—repeated application of constant displacement with variable force. In an SPS protocol, the patient is fitted with an orthosis about the joint. The orthosis is operated to stretch the joint until there is tissue/muscle resistance. The orthosis maintains the joint in this position for a set time period, for example five minutes, allowing for stress relaxation. The orthosis is then operated to incrementally increase the stretch in the tissue and again held in position for the set time period. The process of incrementally increasing the stretch in the tissue is continued, with the pattern being repeated for a maximum total session time, for example 30 minutes. The protocol can be progressed by increasing the time period, total treatment time, or with the addition of sessions per day. Additionally, the applied force may also be increased.

Another treatment protocol uses principles of creep to constantly apply a force over variable displacement. In other words, techniques and devices utilizing principles of creep involve continued deformation with the application of a fixed load. For tissue, the deformation and elongation are continuous but slow (requiring hours to days to obtain plastic deformation), and the material is kept under a constant state of stress. Treatment methods such as traction therapy and dynamic splinting are based on the properties of creep.

SUMMARY OF THE DISCLOSURE

In one aspect, an ankle stretch orthosis generally comprises a foot assembly having a ball support assembly adjustably mounted on a foot plate. The foot assembly comprises an adjustment mechanism configured for selectively adjusting a position of ball support assembly relative to the foot plate to align the ball support assembly with a ball portion of a foot that is one of supinated and pronated.

In another aspect, an orthosis generally comprises a frame including a first body portion securement assembly and a second body portion securement assembly movably connected to the first body portion securement assembly for movement relative to the first body portion securement assembly. A drive assembly is configured to drive movement of the second body portion securement assembly relative to the first body portion securement assembly. The drive assembly comprises an actuation mechanism, a linkage mechanism, and a dynamic force mechanism. The linkage mechanism comprises at least one driving link and a driven link. The driving link is mounted on the first body portion securement member and operatively connected to the actuation mechanism and driving link to transmit a driving force from the actuation mechanism to the driven link to move the driven link relative to the first body portion securement member. The dynamic force mechanism is operatively connected to the driven link and the second body portion securement member to transmit a movement force from the driven link to the second body portion securement member. The dynamic force mechanism is configured to move the second body portion securement assembly relative to the first body portion securement assembly using the movement force until a maximum range of motion of the second body portion securement assembly has been reached and being configured to dynamically impart the movement force upon the second body portion securement assembly after the maximum range of motion has been reached.

BRIEF DESCRIPTION OF THE DRAWINGS

FIG. 2 is a perspective of a frame of the orthosis;

FIG. 3A is a bottom plan view of the orthosis;

FIG. 8 is a perspective similar to FIG. 7 with the drive assembly cover and cap removed to reveal internal components;

FIG. 9 is an exploded view of the drive assembly and portion of the frame; and

Corresponding reference characters indicate corresponding parts throughout the drawings.

DETAILED DESCRIPTION

Figure 1:
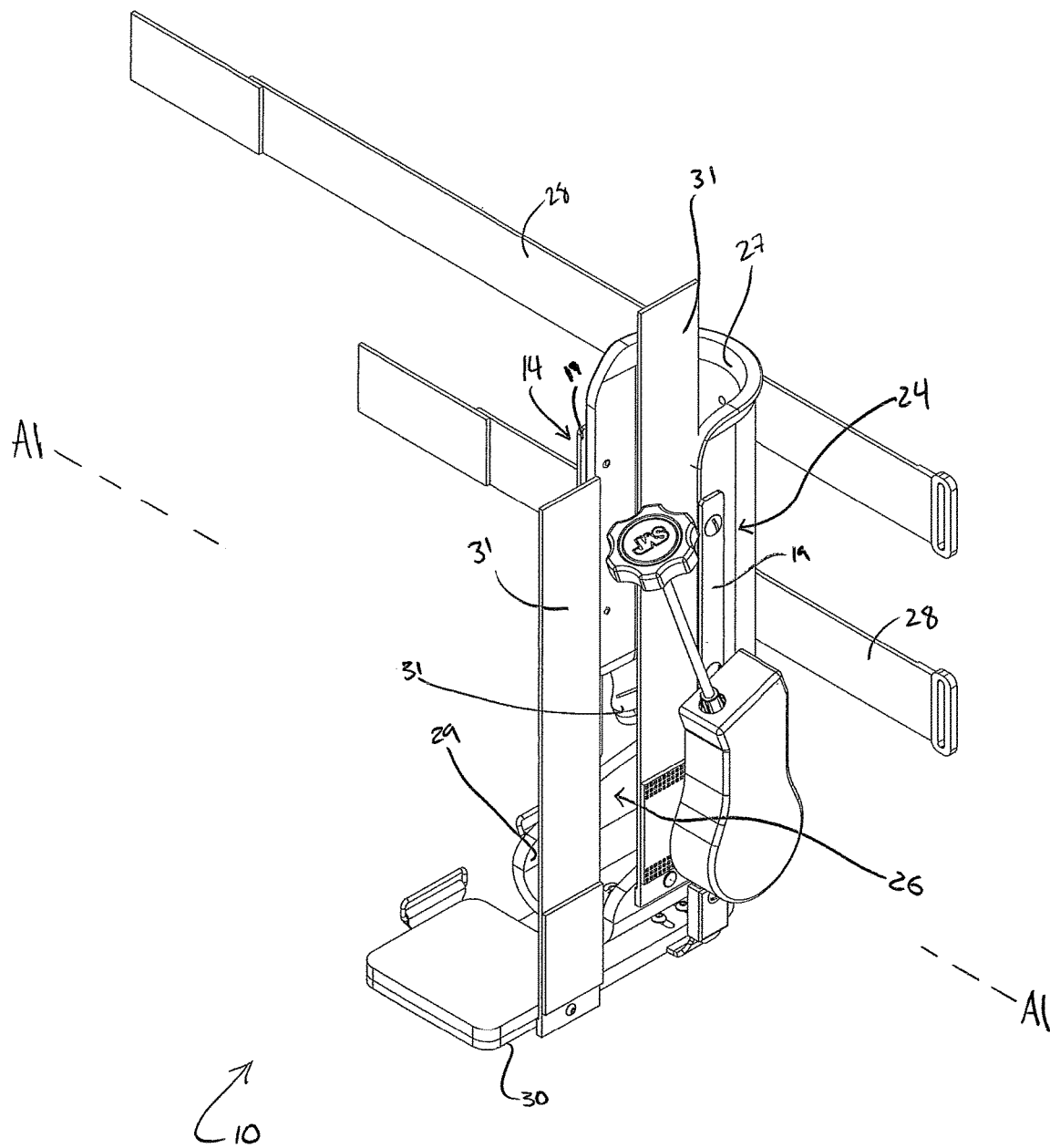
FIG. 1 is a perspective of an orthosis.

Referring to FIG. 1, an orthosis for treating a joint of a subject is generally indicated at reference numeral 10. The general structure of the orthosis 10 is suitable for treating an ankle of the body. In particular, the configuration of the orthosis 10 is suitable for increasing range of motion of the left ankle in plantarflexion, although the orthosis may be suitable for increasing range of motion of the right ankle in plantarflexion. By changing the orientation of various components of the orthosis 10, it could be adapted to increase the range of motion of either ankle in dorsiflexion. Various teachings of the orthosis 10 are also suitable for orthoses for treating other joints, including but not limited to the shoulder joint, radioulnar joint, other hinge joints (e.g., knee joint, elbow joint, etc.), or ellipsoidal joints (e.g., wrist joint, finger joints, toe joints). Thus, in other embodiments the teachings of the illustrated orthosis may be suitable for increasing range of motion of a body joint in adduction and/or abduction, pronation and/or supination, inward and/or outward rotation, flexion and/or extension, etc.

Referring to FIG. 2, the orthosis 10 includes a frame, generally indicated at 14, configured to mount a leg of a body for rotation of the ankle in flexion about an axis of rotation A1. The frame 14 includes a lower leg assembly 16 (broadly, a first body portion securement assembly) and a foot assembly 18 (broadly, a second body portion securement assembly). The illustrated lower leg assembly 16 includes one or more cuff support members 19, for example, the lower leg assembly includes two spaced apart cuff support members from one another on opposite sides of the frame 14. The cuff support members 19 are pivotally connected to one or more foot pivoting members 20 of the foot assembly 18. In the illustrated embodiment, one of the cuff support members 19 (the left support member as shown in FIG. 2) is directly attached to the foot pivoting member 20. A drive mechanism mounting bracket 22 is fixed to the other cuff support member 19 (the right support member as shown in FIG. 2) for rotation relative to the foot pivoting member 20 about the axis A1. The foot pivoting members 20 are fixedly attached to a foot plate 25 for supporting a foot of the body.

Referring to FIG. 1, the cuff support members 19 mount a first cuff, generally indicated at 24, and the foot plate 25 mounts a second cuff, generally indicated at 26. As shown in FIG. 1, the first cuff 24 is a lower leg cuff configured to secure a lower portion of a leg of a body to the orthosis 10. Preferably the cuff 24 secures the lower leg portion of the body above the ankle. The illustrated cuff 24 includes a cuff pad 27 attached to the support members 19 and configured to engage the calf of a body. The cuff 24 also includes a plurality of hook and loop fasteners 28 configured to strap the lower leg portion on the cuff pad 27 to secure the lower leg portion in the cuff. The second cuff 26 is a foot cuff configured to secure the foot of a body to the orthosis 10. The foot cuff 26 includes a padded heel support 29 and an adjustable ball support assembly 30, each of which is mounted on the foot plate 25. As shown in FIG. 1, a plurality of hook and loop fasteners 31 are configured to secure a heel portion of the foot in the heel support 29 and to secure a ball portion of the foot against the ball support assembly 30. As will be discussed in further detail below, the position of the ball support assembly 30 is adjustable to accommodate different sizes and shapes of feet. As shown in FIG. 2, the ball support assembly 30 includes a ball support plate 32 and a ball support pad 34 attached to the ball support plate. As shown in FIG. 3A, a ball support mount 36 is configured to mount the ball support plate 32 and ball support pad 34 to the foot plate 25 in a desired position.

Figure 3B:
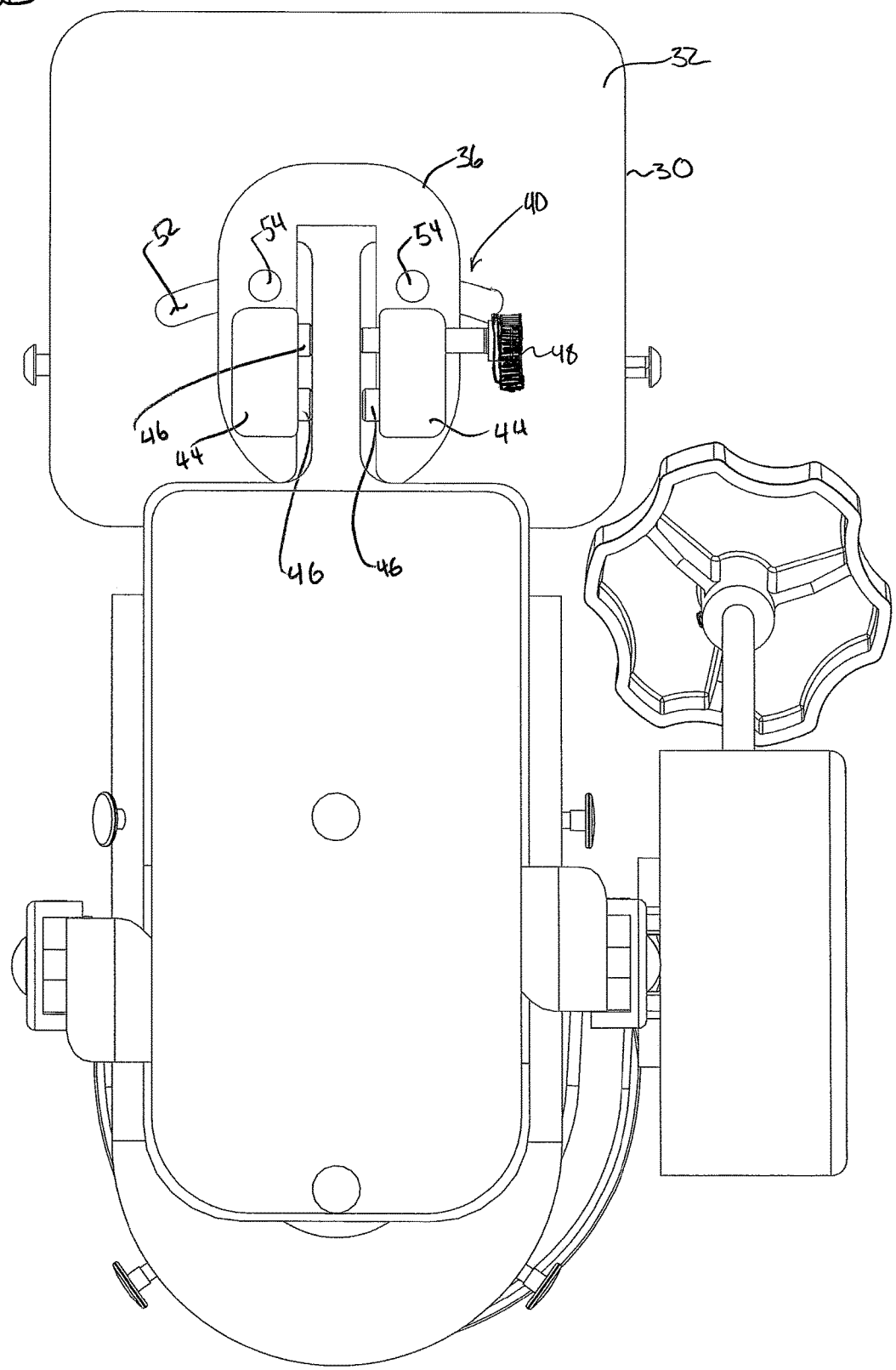
FIG. 3B is like FIG. 3A, but illustrates a ball support assembly in a different axial position.

Referring to FIGS. 3A and 3B, the foot assembly 18 includes an axial ball support adjustment mechanism, generally indicated at 40. In the illustrated embodiment, the foot plate 25 defines an axially extending track 42 at the distal end of the foot plate. The ball support mount 36 includes two spaced apart guide members 44 shaped and arranged to slidably receive the track 42 therebetween. Sliding projections 46 extend inward from the guide members 44 and slidably engage the track 42. A thumb screw 48 (e.g., set screw) is threadably mated with a corresponding hole in one of the guide members 44 (the right guide member as shown in FIGS. 3A, 3B). The thumb screw 48 is configured to be loosened to permit the ball support mount 36 to slide axially along the track 42 (compare FIGS. 3A and 3B) and tightened to secure the ball support mount to the track. The ball support assembly 30 moves generally conjointly with the ball support mount 36 when the ball support mount slides along the track 42 and is fixed in place when the thumb screw 48 fastens the ball support mount to the track.

Figure 4:
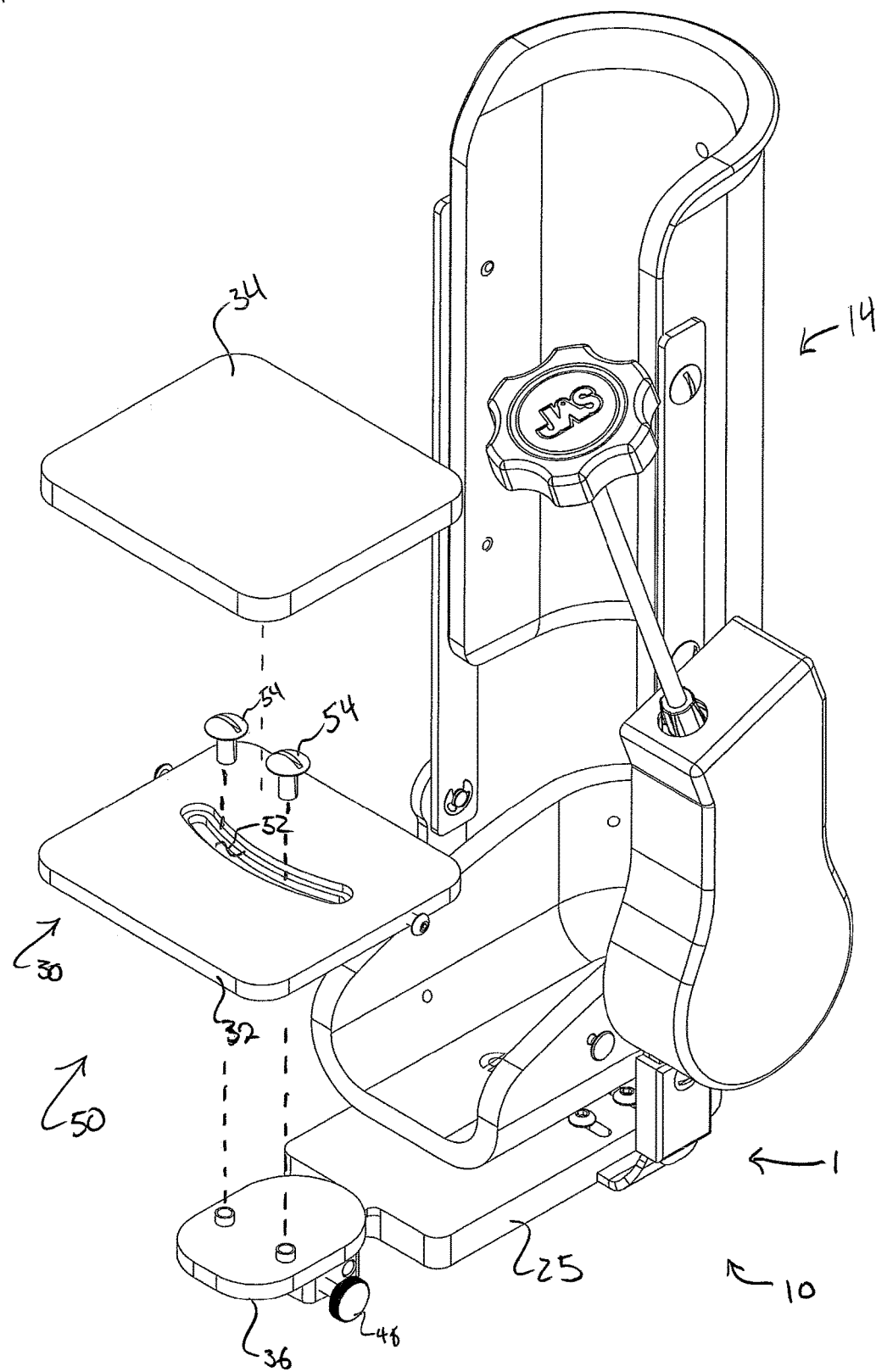
FIG. 4 is a perspective of the frame and a drive assembly of the orthosis with parts of the ball support assembly illustrated in an exploded view.

The foot assembly 18 further includes a pronation/supination adjustment mechanism 50. As shown in FIG. 4, the plate 32 defines an elongate slot 52. Fasteners 54 (e.g., bolts) are configured to extend through the slot and selectively fasten the ball support plate 32 to the ball support mount 36. In the illustrated embodiment two bolts 54 are threadably received in mating holes in the ball support mount 36. Any number and types of fasteners can be used to selectively secure the ball support plate to the ball support mount without departing from the scope of the invention. When the bolts 54 are loosened, the ball support plate 32 can move relative to the ball support mount 36 and the heel support 29, with the bolts 54 sliding through the elongate slot 52, to adjust the position of ball support assembly 30 relative to the ball support mount and the heel support to suit the pronation or supination of a particular foot. The ball support assembly 30 is selectively movable generally in medial and lateral directions, which is in a direction that is generally transverse to an anterior-superior axis of the heel support 29. In the illustrated embodiment, the elongate slot 52 is slightly curved or arcuate, such that the ball support assembly 30 also moves slightly in a posterior direction as it moves from its neutral position (as shown in FIG. 3A, for example) in either one of the medial and lateral directions. Thus, in the illustrated embodiment, the ball support assembly 30 extends at an offset angle (i.e., not aligned) relative to the anterior-superior axis of the heel support 29. The elongate slot 52 is also counter sunk to receive the heads of the bolts 54 below the top surface of the ball support plate 32. Preferably, the ball pad 34 is selectively removable to allow for loosening and tightening of the bolts 54. The ball support assembly 30 can support the ball portion of a user's foot with the bolts 54 partially loosened to allow the ball plate 32 and pad 34 to "float" (e.g., move medially and laterally) to automatically adjust it position, as set forth above, for pronation or supination of the foot during use of the orthosis 10. The bolts 54 can also be tightened prior to use to fix the ball support plate 32 and support pad 34 relative to the foot plate 25.

Referring to FIG. 2, the foot assembly 18 is selectively rotatable relative to the lower leg assembly 16 about the axis A1 in first and second directions P and D. When a leg is received in the orthosis 10 and the foot assembly 18 rotates in the first direction P relative to the lower leg assembly 16, the ankle rotates in plantarflexion direction. When a leg is received in the orthosis 10 and the foot assembly 18 rotates in the second direction D relative to the lower leg assembly 16, the ankle rotates in dorsiflexion direction.

Figure 5:
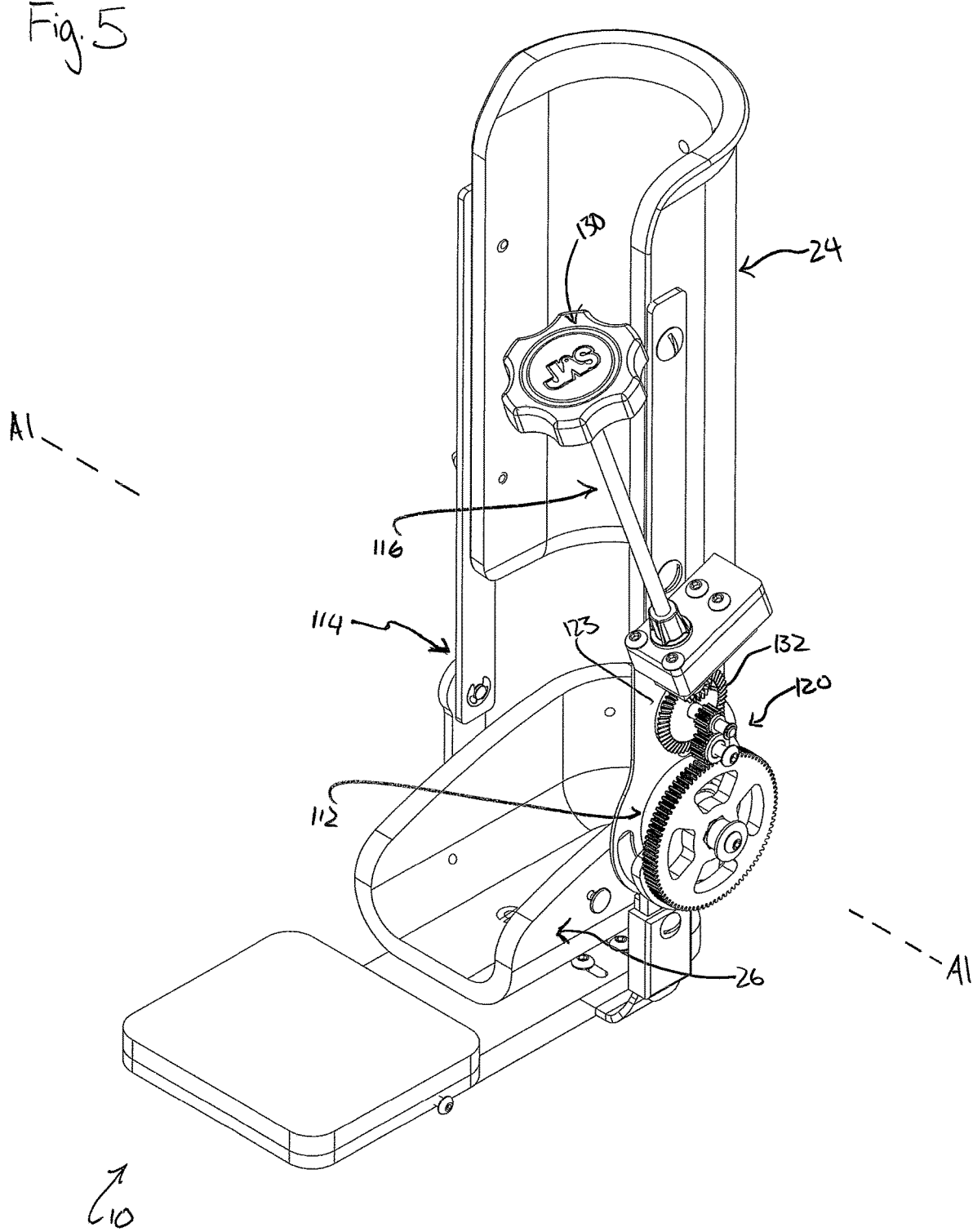
FIG. 5 is a perspective of the frame and drive assembly with a drive assembly cover removed to reveal internal components.

Referring to FIG. 5, the illustrated orthosis 10 is a dynamic stretch orthosis comprising a dynamic force mechanism, generally indicated at 112, for applying a dynamic stretch to an ankle in plantarflexion. An actuator mechanism, generally indicated at 116, is operatively connected to a linkage mechanism, generally indicated at 120, for transmitting force to the dynamic force mechanism 112, as will be explained in further detail below. The rotational linkage mechanism 120 and dynamic force mechanism 112 are each operatively connected to the lower leg assembly 16 and foot assembly 18 to rotate the foot assembly relative to the lower leg assembly about the axis of rotation A1. As explained in further detail below, the illustrated orthosis 10 is configured to drive the linkage mechanism 20 to rotate the lower leg and foot assemblies 16, 18 relative to one another about the axis of rotation A1 to rotate an ankle in flexion until a maximum range of motion of the ankle has been reached; at which point, the orthosis 10 is configured to further drive a link in the linkage mechanism to impart a dynamic force upon the ankle, which urges further flexion of the ankle, thereby increasing the range of motion of the ankle.

As will be apparent from this disclosure, when the first and second cuffs 24, 26 are properly secured to a leg and foot, the orthosis 10 can be used to stretch the corresponding ankle in flexion. Moreover, the orthosis 10 may be used as a combination dynamic and static-progressive stretch orthosis. It is understood that in other embodiments, the dynamic force mechanism may be omitted without departing from the scope of the invention, thereby making the orthosis suitable as a static stretch or static progressive stretch orthosis by using the illustrated actuator mechanism and/or the linkage mechanism. In addition, it is understood that that in other embodiments the orthosis may include the illustrated dynamic force mechanism, while omitting the illustrated actuator mechanism and/or linkage mechanism.

Figure 6:
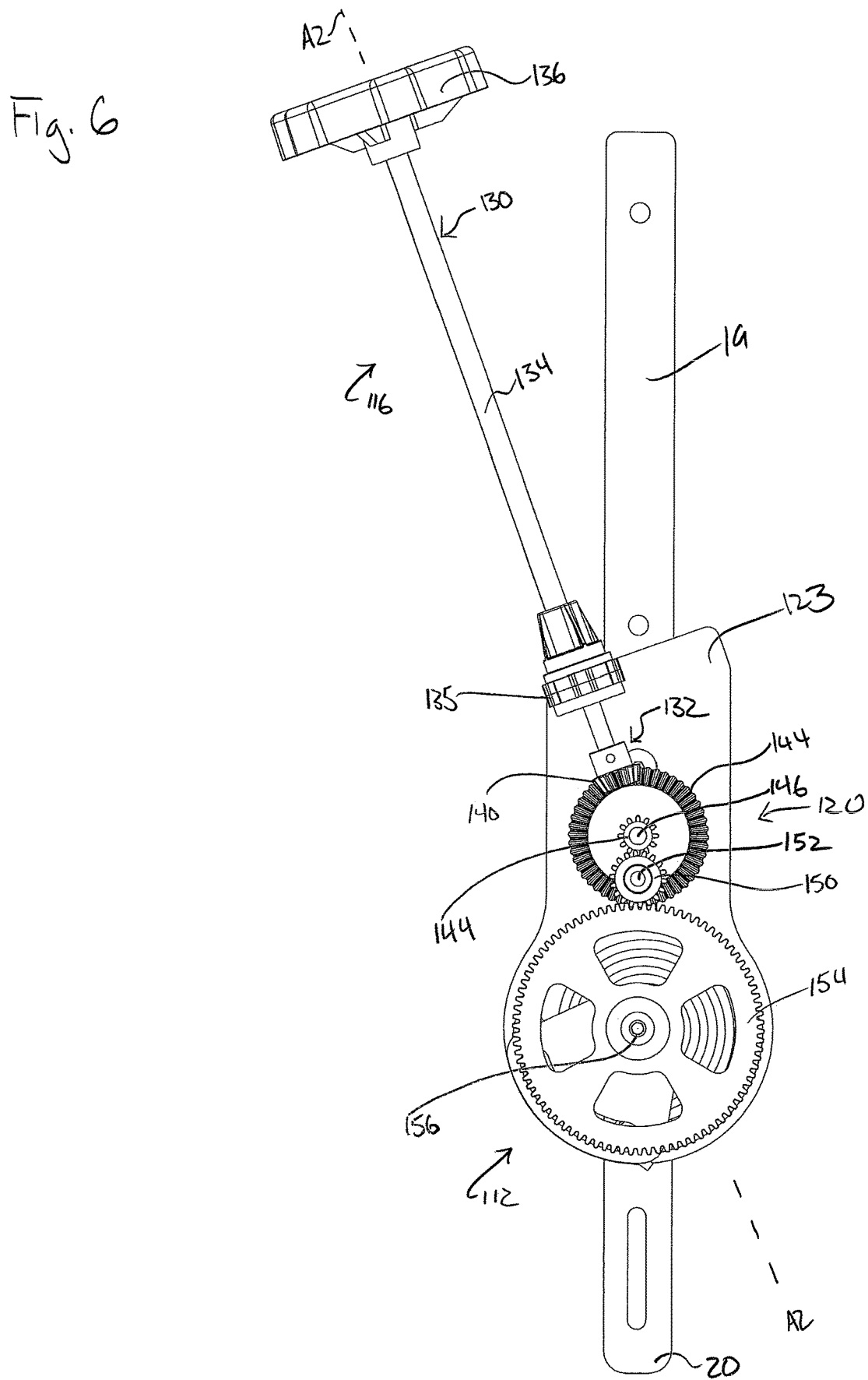
FIG. 6 is an elevation of the drive assembly mounted on a portion of the frame with the drive assembly cover and a drive assembly cap removed to reveal internal components.
Figure 7:
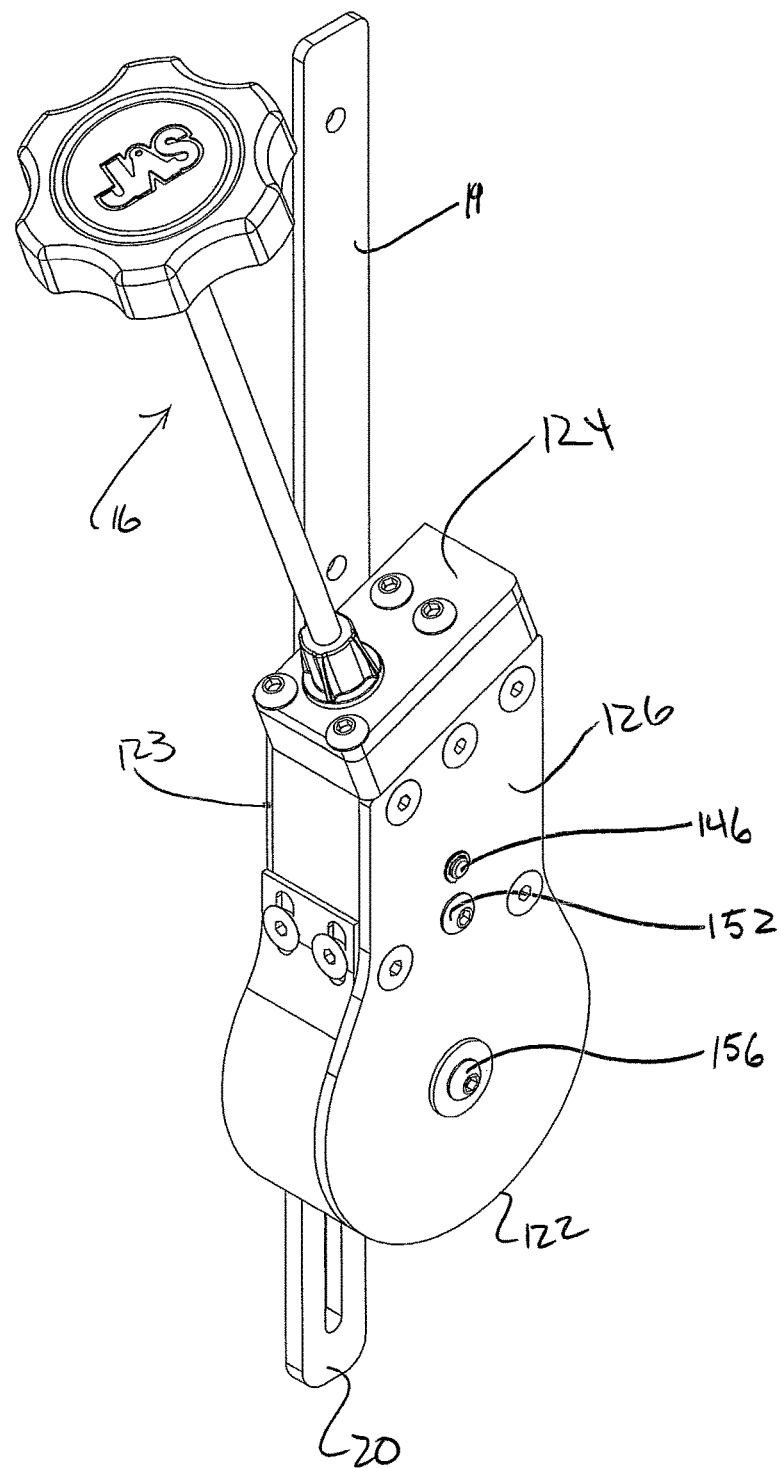
FIG. 7 is a perspective of the drive assembly mounted on the portion of the frame.

As shown in FIG. 1, various components of the actuator mechanism 114, linkage mechanism 120, and dynamic force mechanism 112 are enclosed in a drive assembly housing 122 (FIG. 7). The drive assembly housing 122 also functions to mount various components for rotation. As shown in FIG. 6, the drive assembly housing 122 includes a base plate 123 secured to the drive assembly mounting member 22 of the frame 14. As shown in FIG. 7 an actuator support cap 124 and an outer cover member 126 are mounted on the base plate 123 to enclose the drive assembly.

Referring to FIG. 6, the actuator mechanism 116 is configured to drive movement of the linkage mechanism 120. The actuator mechanism 116 includes a drive assembly, generally indicated at 130, and a transmission assembly, generally indicated at 132. In the illustrated embodiment, the drive assembly 130 includes an input shaft 34 operatively connected to the transmission assembly 132 and an actuator knob 136. The knob 136 and input shaft 134 are configured to be conjointly rotated about a drive axis A2 to drive rotation of the transmission assembly 132. The input shaft 134 extends through a rotational bearing 135 in the actuator support cap 124 (FIG. 7) of the drive assembly housing 122. The bearing 135 and support cap 124 mount the input shaft 134 for rotation about the drive axis A2. The knob 136 is configured to be grasped by a user who rotates the drive assembly 310. But in other embodiments, the input shaft could be operatively connected to a prime mover, such as a motor or engine, for rotating the input shaft.

In the illustrated embodiment, the transmission assembly 132 comprises a bevel pinion gear 140 that is received for rotation within the drive assembly housing 122. The bevel pinion gear 140 is operatively connected to the input shaft 134 and is configured to rotate conjointly with the input shaft about the drive axis A2. The bevel pinion gear 140 operatively meshes with a mating bevel ring gear 144 to drive movement of the linkage mechanism 120.

Referring to FIGS. 8, 9, the linkage mechanism 20 includes the bevel ring gear 144 (broadly, a first driving link or first driving gear). A pin 146 mounts the bevel ring gear 144 on the drive assembly housing 122 for rotation about an axis of rotation A3. In the illustrated embodiment, the pin 146 is rotatably secured to the frame 14 and cover 126 of the drive assembly housing 122. The bevel ring gear 144 is indexed to the pin 146 so that the pin rotates conjointly with the bevel ring gear about the axis A3. The pin 146 also mounts a first spur gear (broadly, a second driving link or second driving gear) for conjoint rotation with the pin 146 and bevel ring gear 144 about the axis A3. The first spur gear 148 operatively meshes with a second spur gear 150 (broadly, a third driving link or third driving gear). A pin 152 mounts the second spur gear 150 to the cover 126 of the drive assembly housing 122 for rotation about an axis of rotation A4. The second spur gear 150 operatively meshes with a third spur gear 154 (broadly, a driven link or driven gear) configured for rotation about the axis of rotation A1. The bevel ring gear 144, first spur gear 148, and second spur gear 150, form a driving linkage assembly that is operatively connected between the actuation mechanism 116 and driven gear 154 to receive a rotational force from the actuation mechanism and transmit the rotational force to the driven gear. A pin 156 is mounted on the drive assembly housing 122 for rotation relative to the drive assembly housing about the axis of rotation A1. The third spur gear 154 is indexed to the pin 156 so that the pin rotates conjointly with the gear about axis of rotation A1.

Referring to FIG. 8, when the input shaft 134 of the actuation mechanism 116 is rotated in a first direction R1 about the drive axis A2, the bevel pinion gear 140 rotates the bevel ring gear 144 and first spur gear 148 about the axis of rotation A3 in a first direction R2. The first spur 148 gear drives the second spur gear 150 to rotate about the axis of rotation A4 in a first direction R3, and the second spur gear drives the third spur gear 154 to rotate about the axis of rotation A1 in a first direction R4. As will be discussed in further detail below, the driven gear 154 is configured to rotate the foot assembly 18 in the plantarflexion direction P relative to the lower leg assembly 16 when it rotates in the first direction R4. When the input shaft 134 of the actuation mechanism 116 is rotated in a second direction R5 about the drive axis A2, the bevel pinion gear 140 rotates the bevel ring gear 144 and first spur gear 148 about the axis of rotation A3 in a second direction R6. The first spur gear 148 drives the second spur gear 150 to rotate about the axis of rotation A4 in a second direction R7, and the second spur gear drives the third spur gear 154 to rotate about the axis of rotation A1 in a second direction R8. As will be discussed in further detail below, the driven gear 154 is configured to rotate the foot assembly 18 in the dorsiflexion direction D relative to the lower leg assembly 16 when it rotates in the second direction R8.

The components of the rotational linkage mechanism 120 rotate about their respective axes of rotation A1, A3, A4 relative to the drive assembly housing 122. As discussed above, the drive assembly housing is fixed to the lower leg assembly 16 of the orthosis frame 14. Moreover, as will be discussed in further detail below, the dynamic force mechanism 112 operatively connects the driven spur gear 154 to the foot assembly 18. As a result, rotation of the driven spur gear 154 in the first and second directions R4, R8 imparts a rotational force on the dynamic force mechanism 112 that it, in turn, transmits to the foot assembly 18. The dynamic force mechanism 112 is configured to operate in a static loading mode and dynamic loading mode. In the static loading mode, the dynamic force mechanism 112 transmits the rotational force from the driven gear 154 to the foot assembly 18 to rotate the foot assembly relative to the lower leg assembly 16 about the axis of rotation A1. In the dynamic loading mode, the foot assembly 18 is prevented from rotating relative to the lower leg assembly 16 by, for example, an ankle of a leg received in the orthosis 10 reaching a maximum range of motion. So instead of statically rotating the orthosis, the dynamic force mechanism 112 dynamically transmits a rotational force to the foot assembly 18 to urge the foot assembly to rotate further about the axis of rotation A1 relative to the lower leg assembly 16.

Referring to FIG. 9, the dynamic force mechanism 112 includes a spring 160, a stop 162, and connector 164 for operatively connecting the spring 160 to the foot assembly 18. In the illustrated embodiment, the elastic spring 160 is a clock spring, but other types of springs that is an elastic body or device that recovers its original shape when released after being distorted and configured to impart a dynamic force between a driven member of a linkage mechanism and a body portion supporting assembly of an orthosis frame may also be used without departing from the scope of the invention. An inner end of the clock spring 160 is attached to the pin 156 to rotate conjointly with the pin about the axis A1. The connector 164 operatively connects the outer end of the spring 160 to the foot assembly 18. In the illustrated embodiment, the connector 164 is a shaft attached to and extending outward from the foot pivoting member 20. The shaft 164 extends through a curved slot 166 in the base plate 123 of the drive assembly housing 122. In the static loading mode, the spring 160 rotates with the pin 156 to rotate the connector 164 and foot assembly 18 about the axis A1. As the connector 164 pivots about the axis of rotation A1, it travels through the slot 166 in the base plate 123.

In the dynamic loading mode, the spring 160 deforms against a holding force imparted by the foot assembly 18 on the connector 164 as the driven gear 154 rotates the pin 156 about the axis of rotation A1. The deformed spring 156 imparts a dynamic force on the connector 164 in the same direction that the driven gear 154 has rotated relative to the foot assembly 18, thereby urging the foot assembly further in the direction of rotation. In the illustrated embodiment, the spring 160 is oriented to deform against rotation of the driven gear 154 relative to the foot assembly 18 in the first direction R4 (e.g., when an ankle has reached a maximum range of motion in plantarflexion). But by reversing the arrangement of the dynamic force mechanism 120, the spring could be arranged to deform against rotation of the driven gear when it rotates relative to the foot assembly in the second direction R8 (e.g., against an ankle that has reached a maximum range of motion in dorsiflexion).

Referring again to FIG. 9, the stop 162 is configured to limit the deformation of the spring 160 in the dynamic loading mode. In the illustrated embodiment the stop 162 is a generally triangularly shaped plate that is indexed for rotation with the pin 156. The plate 162 defines a curved elongate slot 168 for slidably receiving the connector 164 therein. In the static loading mode, the connector 164 is positioned near a first end 168A of the slot. When the dynamic force mechanism 112 enters the dynamic loading mode, the plate 162 rotates with the pin 156 relative to the connector 164 as the connector remains fixed to the foot assembly 18. The connector 164 travels through the slot 168 toward an opposite second end 168B. When the connector 164 engages the second end 168B of the slot, the plate 162 inhibits further rotation of the plate relative to the connector 164. Since the plate 162 is indexed to the pin 156, along with the driven gear 154, the plate stops further rotation of the pin and driven gear as well, thereby preventing further driving of the linkage assembly 120. Although the illustrated embodiment uses a plate defining a curved slot to limit the loading of the dynamic force mechanism in the dynamic loading mode, other embodiments can use limiters that limit loading of a spring in a dynamic loading mode in other ways without departing from the scope of the invention.

An exemplary method of using the orthosis 10 will now be briefly described. Before loading a subject's leg into the orthosis 10, the axial ball support adjustment mechanism 40 and pronation/supination adjustment mechanism 50 can be adjusted to properly position the ball support assembly 30 for the subject's foot. If desired, the fasteners 54 of the pronation/supination adjustment mechanism 50 can be left in a partially loosened state to allow the ball support assembly 30 to self-adjust for pronation or supination of the foot during use. Otherwise, the fasteners 54 and thumb screw 48 are tightened to fix the ball support assembly 30 in place with respect to the foot plate 25.

Figure 10A:
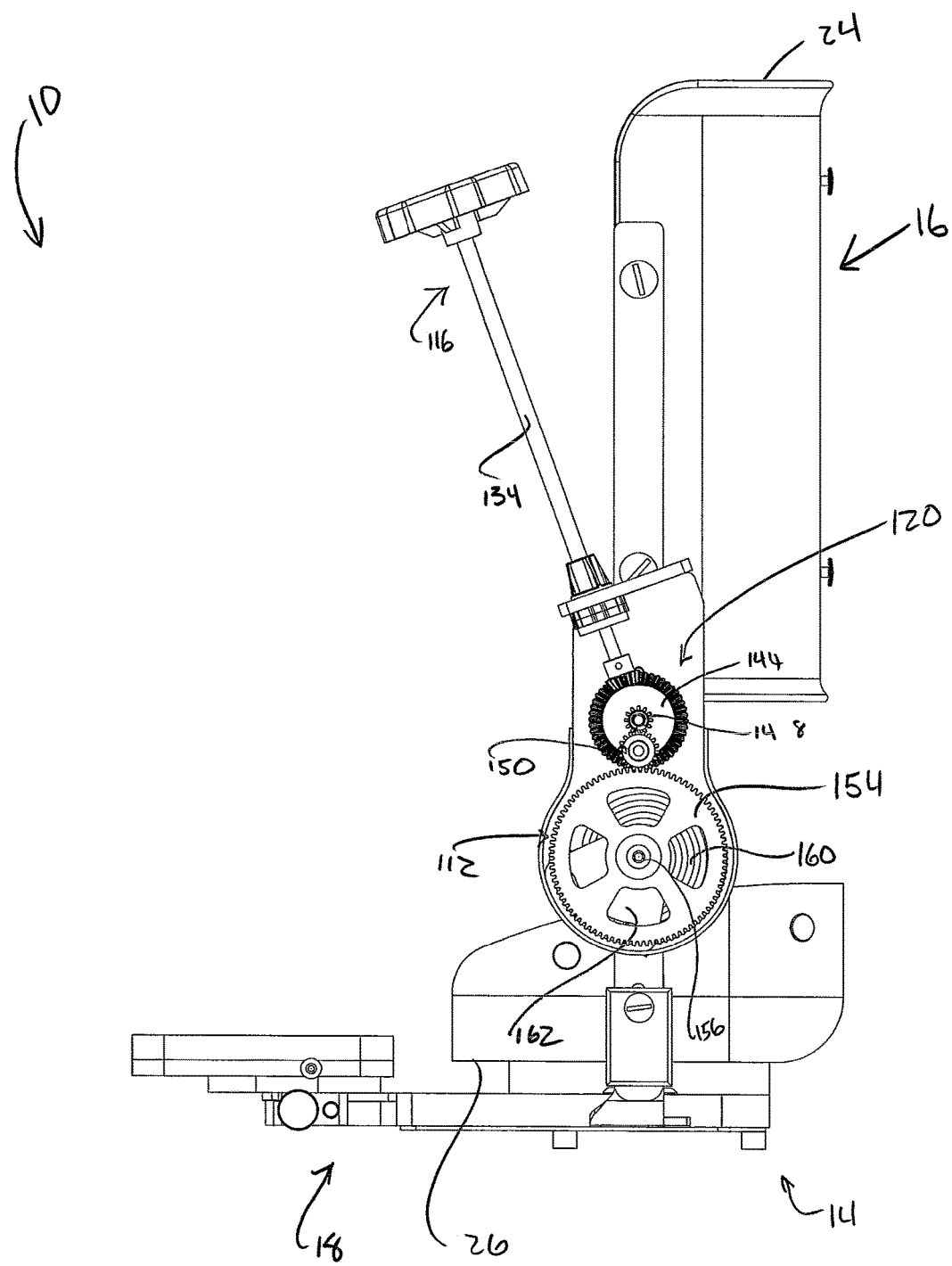
FIGS. 10A-13B are elevations of the orthotic with straps and a drive assembly cover removed illustrating various locations of internal components of the drive assembly at various stages during in an exemplary use of the orthosis, wherein the Figures have figure numbers ending with the designation 'B' are the same as corresponding figure numbers ending with the designation 'A' with a driven gear removed to reveal additional components.
Figure 10B:
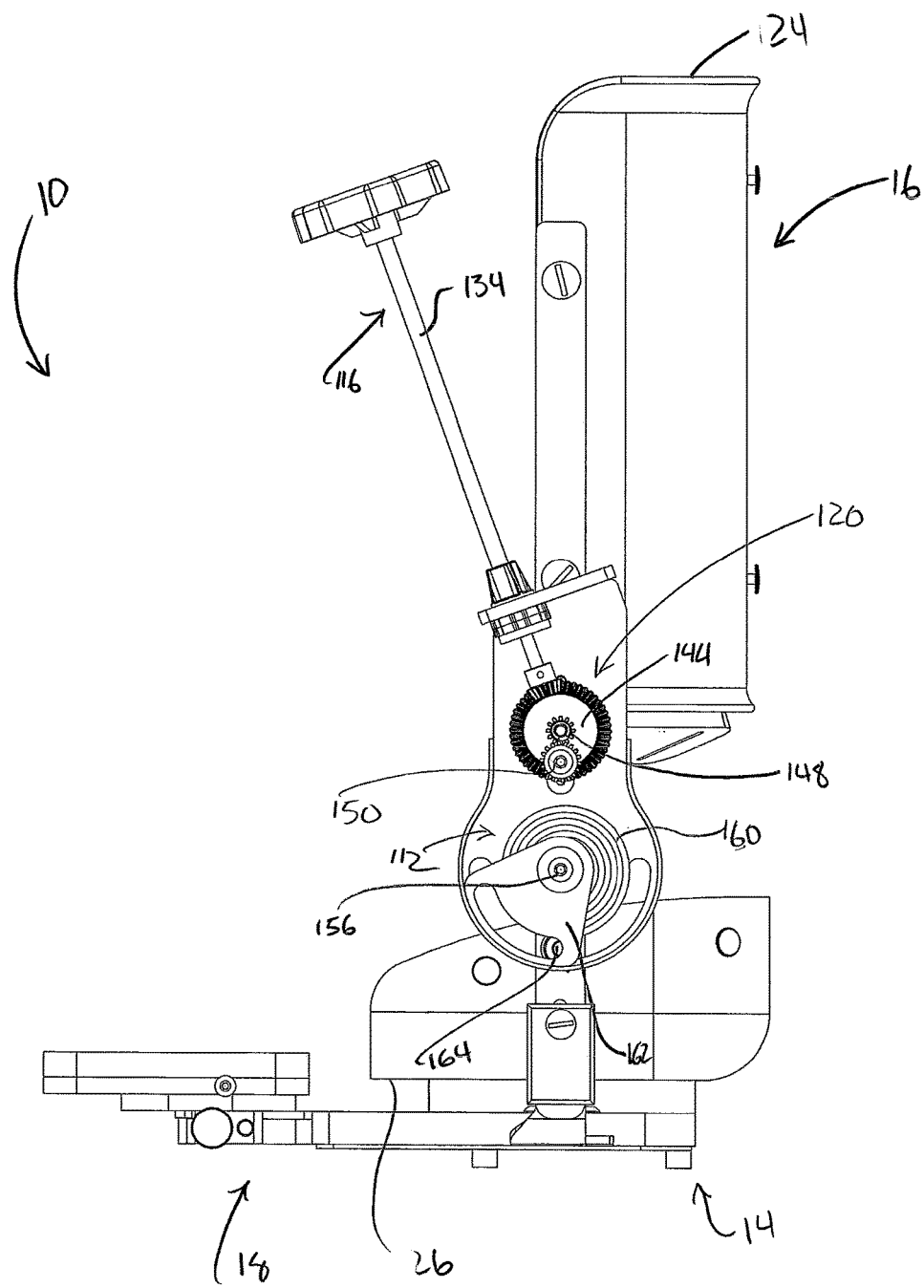

A subject's leg is mounted in the orthosis 10 so that a lower leg portion is received in the cuff 24 and a foot is received in the cuff 26. The cuffs 24, 26 are tightened to operatively secure the lower leg portion to the lower leg frame assembly 16 and the foot to the foot frame assembly 18. A suitable initial position for installing the subject's leg in the orthosis 10 is illustrated in FIGS. 10A-10B. Other initial positions may also be used without departing from the scope of the invention.

With the leg properly installed in the orthotic 10, the actuation mechanism 116 is actuated to drive the linkage mechanism 120. For example, to rotate the foot assembly 18 relative to the lower leg assembly 20 in the plantarflexion direction P, the input shaft 134 is rotated about the drive axis A2 in the first direction R1. To rotate the foot assembly 18 relative to the lower leg assembly 20 in the dorsiflexion direction R, the input shaft 134 is rotated about the drive axis A2 in the second direction R5. Preferably, the orthosis 10 initially positions the ankle comfortably, so that it can freely rotate away from the initial position in the plantarflexion and dorsiflexion directions.

Figure 11A:
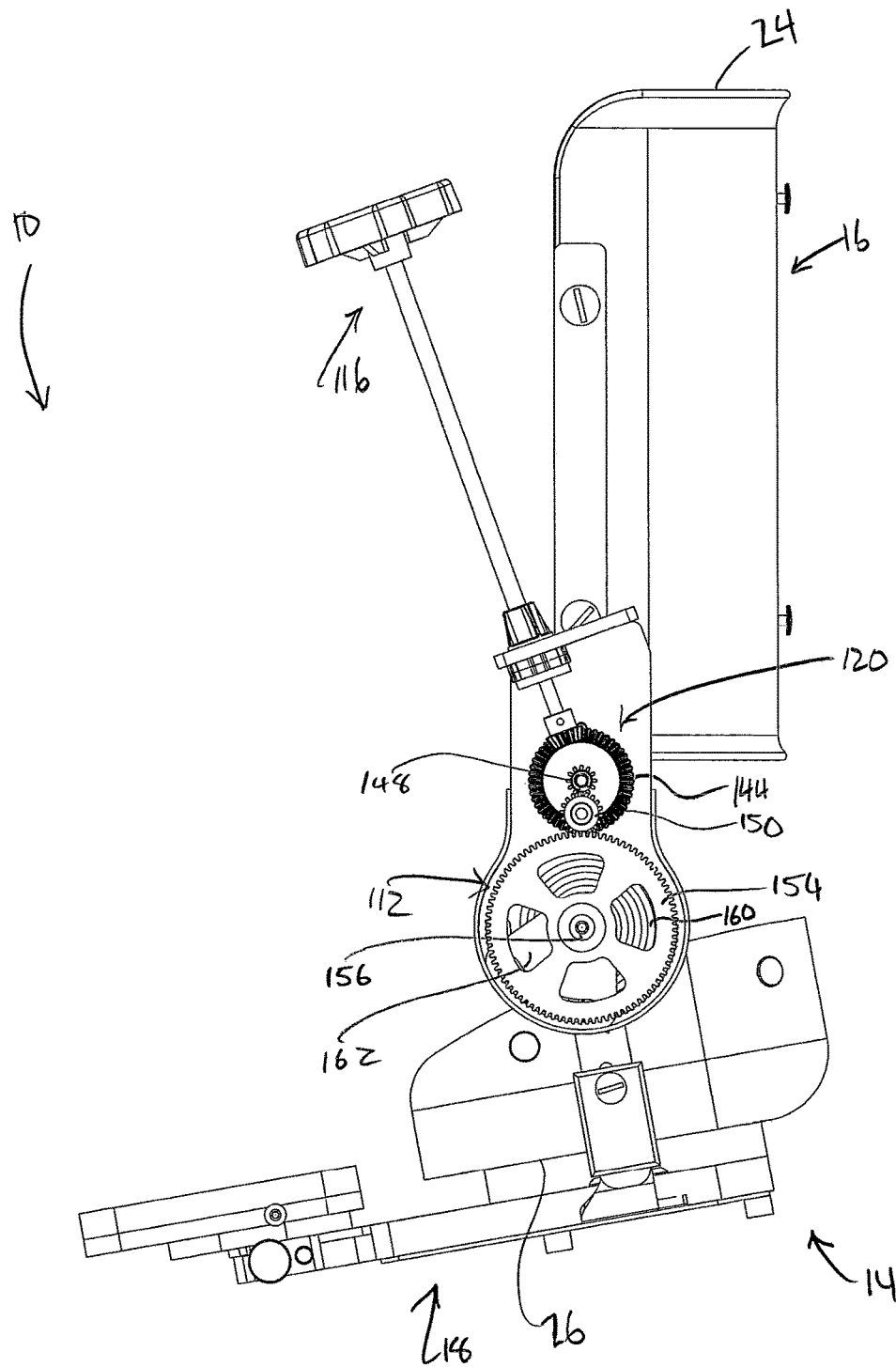
Figure 11B:
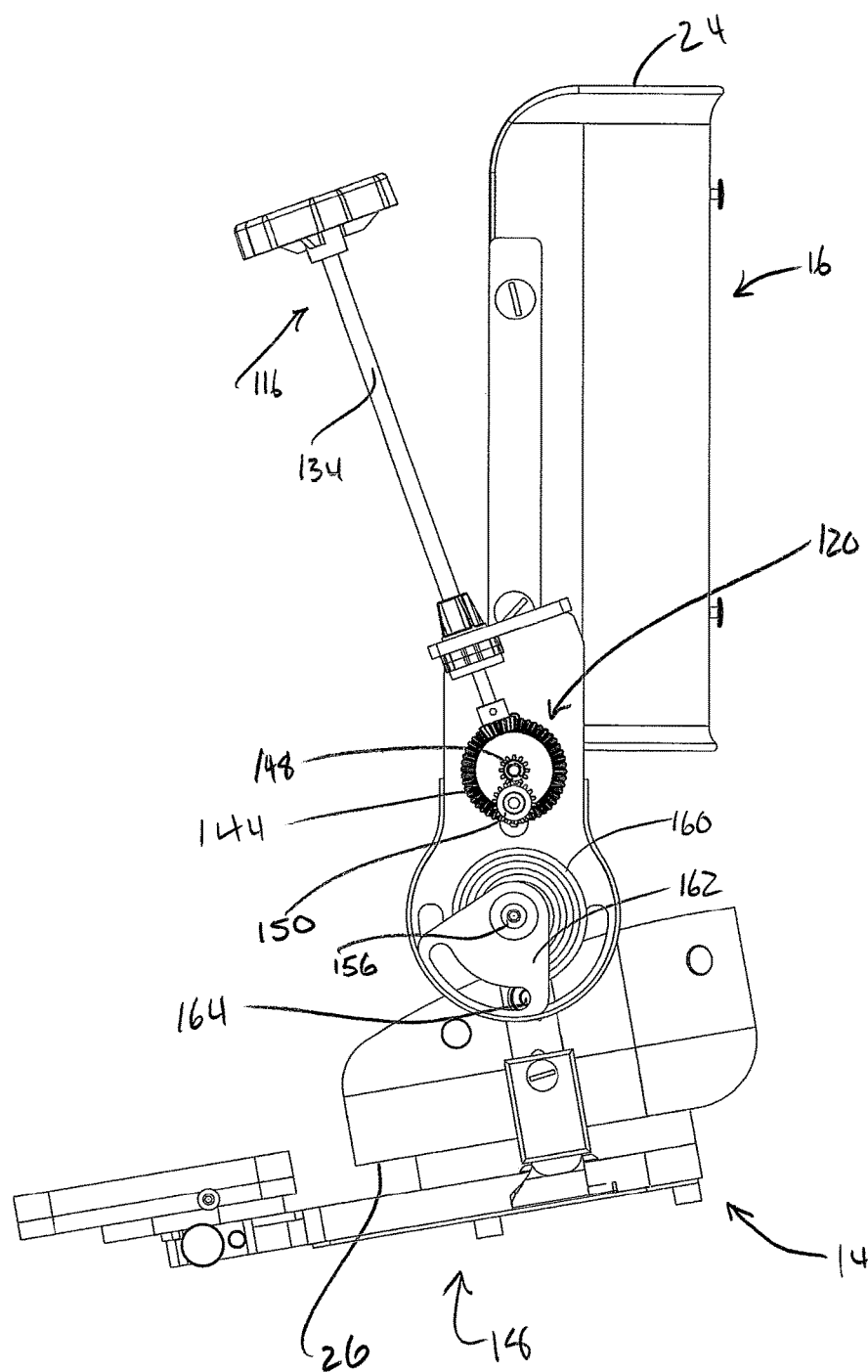

As shown in FIGS. 11A-11B, if the actuation mechanism 116 is rotated in the first direction R1, the bevel ring gear 144 and first spur gear 148 rotate in the first direction R2 about the axis A3, the second spur gear 150 rotates in the first direction R3 about the axis A4, and the driven gear 154 rotates in the first direction R4 about the axis A1. The rotation of the driven gear 154 rotates the pin 156, spring 160, and stop 162. The spring 160 transmits a rotational force upon the connector 164, which urges the foot assembly 18 to rotate about the axis A1 in the plantarflexion direction P. Since the ankle is initially rotating within its maximum range of motion, the foot assembly 18 rotates freely without deforming the spring 160. Thus, in the static loading mode, the dynamic force mechanism 112 transmits the rotational force from the driven gear 154 to the foot assembly 18 to rotate the foot assembly relative to the lower leg assembly 16 in the plantarflexion direction P.

Figure 12A:
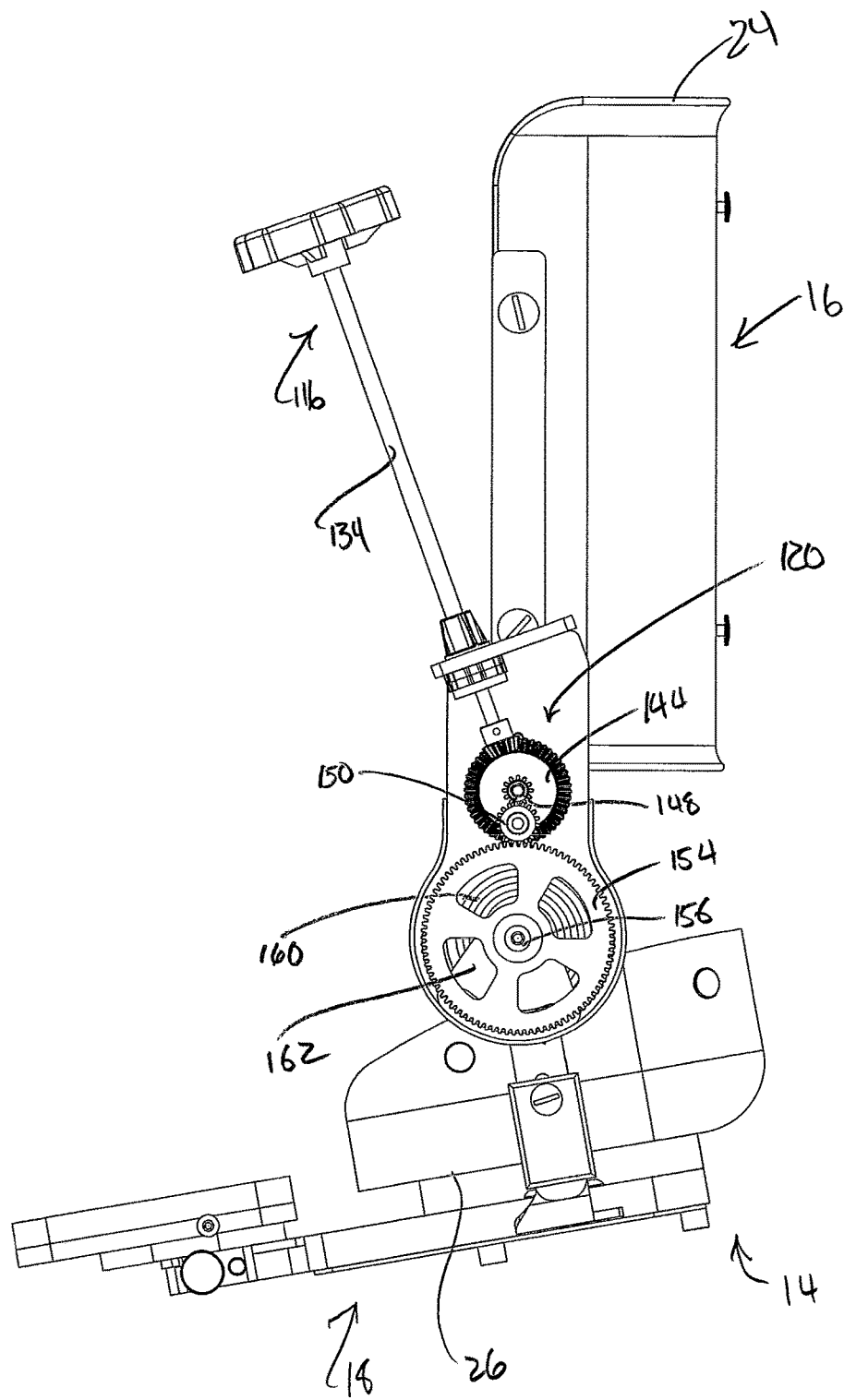
Figure 12B:
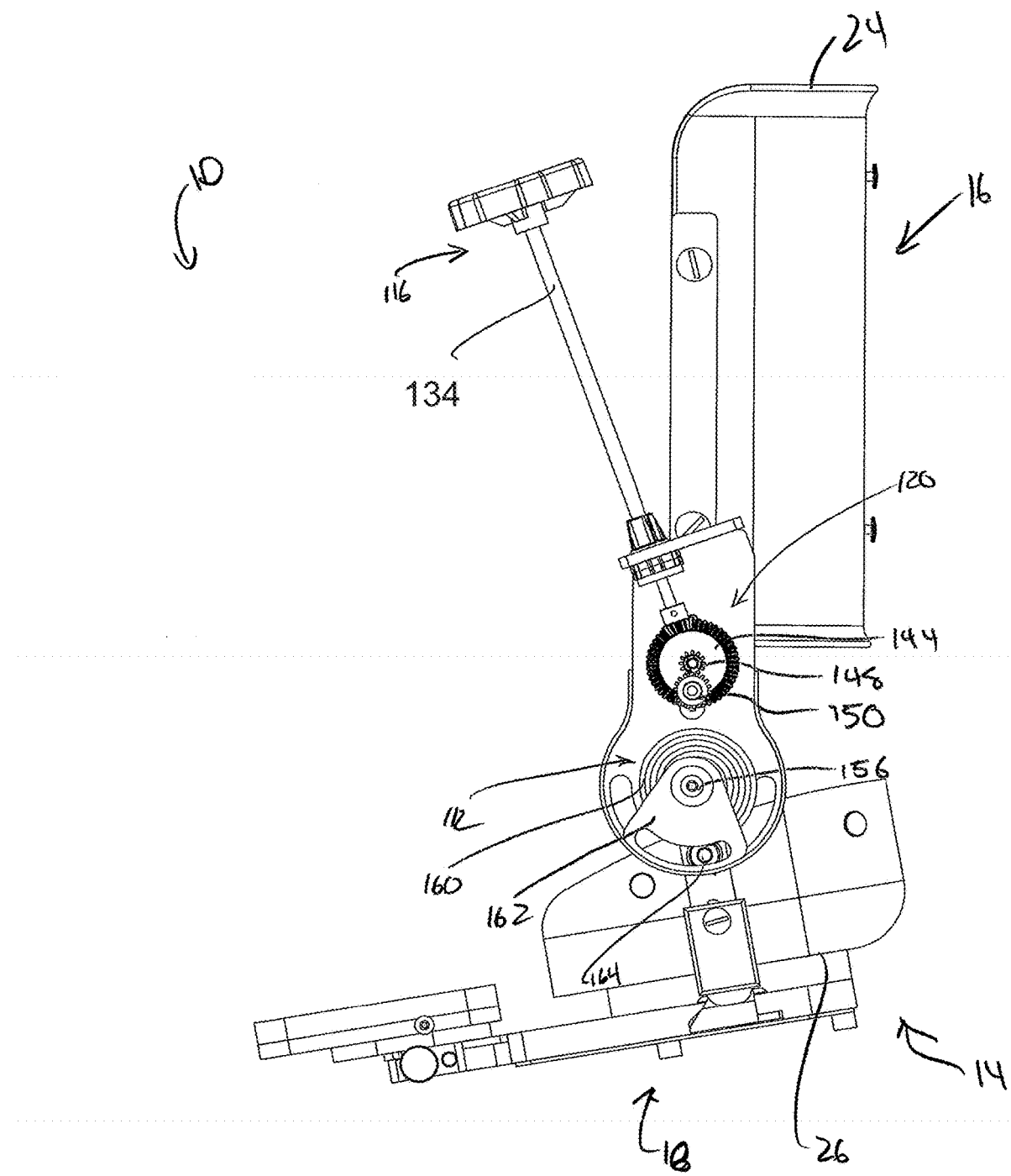

Assuming the position of the orthotic 10 in FIGS. 11A and 11B corresponds with a maximum range of motion of an ankle in plantarflexion, further rotation of the actuation mechanism 116 in the first direction R1 causes the dynamic force mechanism 120 to operate in the dynamic loading mode, as shown in FIGS. 12A-12B. As the actuation mechanism 116 is rotated further in the first direction R1, the bevel ring gear 144 and first spur gear 148 rotate in the first direction R2 about the axis A3, the second spur gear 150 rotates in the first direction R3 about the axis A4, and the driven gear 154 rotates in the first direction R4 about the axis A1. The rotation of the driven gear 154 rotates the pin 154, the inner end of the spring 160, and stop 162 in the first direction R4. But since the ankle prevents the foot assembly 18 from rotating further in the plantarflexion direction P, the connector 164 is prevented from rotating about the axis of rotation A1. As the stop 162 rotates about the axis A1 relative to the connector 164, the connector travels through the slot 168 from the first end 168A toward the second end. If the actuation mechanism 116 is rotated in the first direction R1 until the second end 168B of the stop 168 engages the connector, the engagement prevents further rotation of the linkage mechanism 120 and actuation mechanism 116.

Figure 13A:
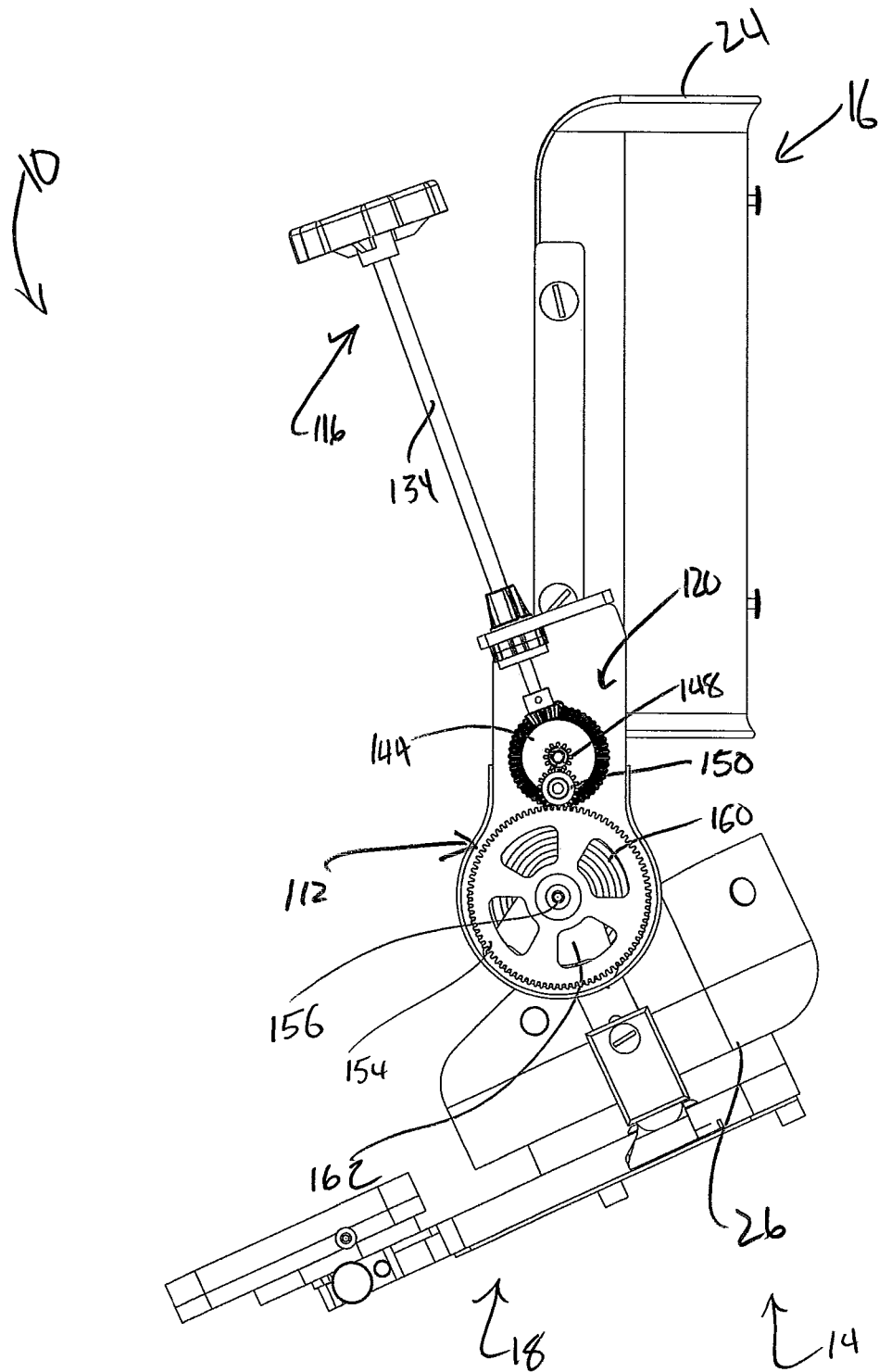
Figure 13B:
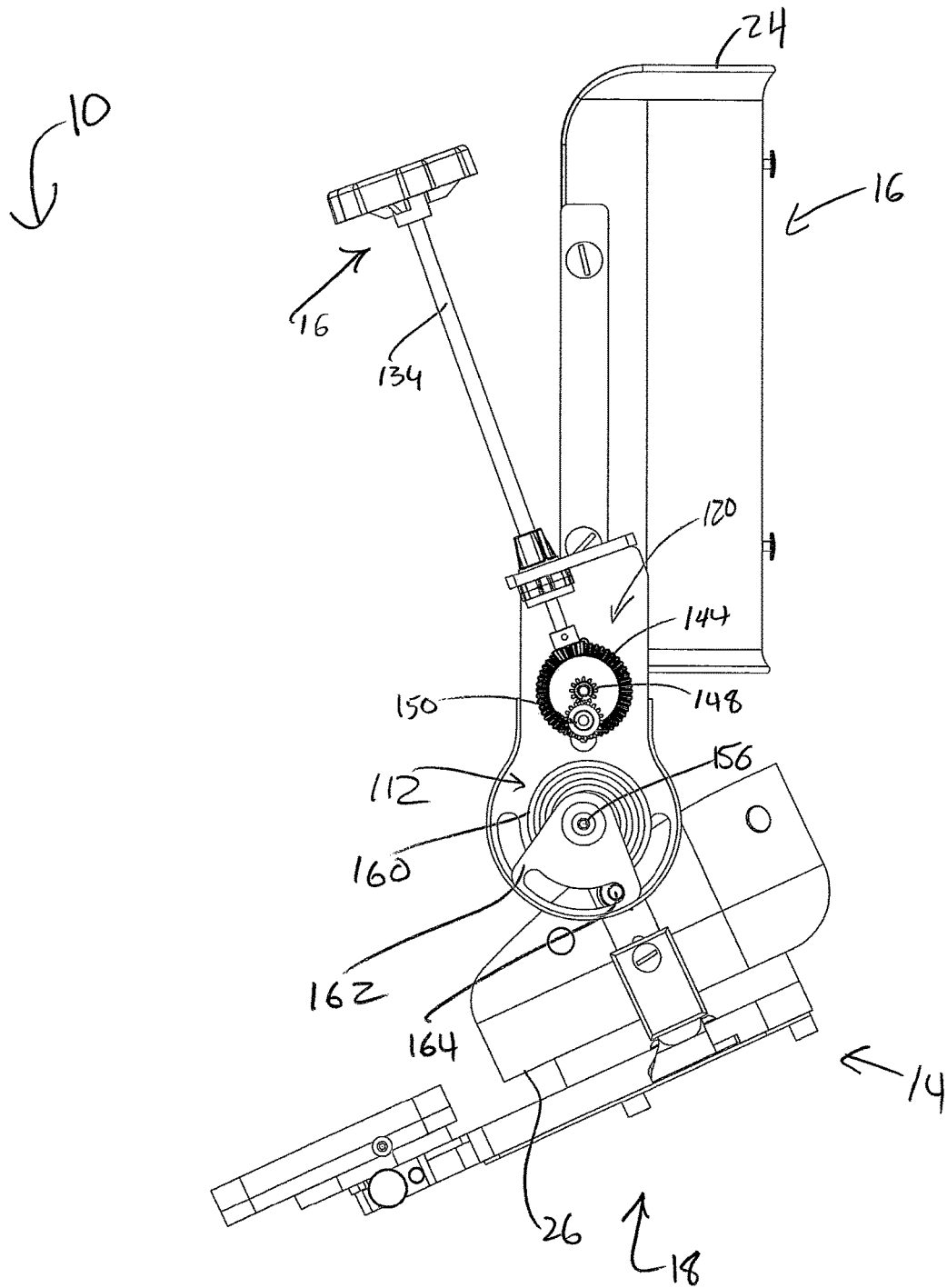

As the pin 156 rotates and the connector 164 remains fixed, the inner end of the spring 160 rotates relative to the outer end of the spring, causing deformation. The deformed spring 160 imparts a dynamic force upon the connector 164, dynamically urging the connector toward rotation about the axis A1 in the direction R4. The dynamic rotational force applied on the connector is transmitted through the foot assembly 18 to the subject's ankle. As shown in FIGS. 13A-13B, the dynamic force continually applied on the ankle eventually causes further plantarflexion beyond the initial maximum range of motion. The foot assembly 18 gradually rotates relative to the lower leg assembly 16 in the plantarflexion direction P, causing the connector 164 to rotate further in the direction R1 and lessening the deformation of the spring 160. By stretching the ankle in plantarflexion beyond its maximum range of motion using dynamic loading, the range of motion is extended.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An orthosis comprising:
a frame including a first body portion securement assembly and a second body portion securement assembly movably connected to the first body portion securement assembly for movement relative to the first body portion securement assembly; and
a drive assembly configured to drive movement of the second body portion securement assembly relative to the first body portion securement assembly comprising:
an actuation mechanism configured to actuate the drive assembly;
at least one driving link and a driven link, the driving link being mounted on the first body portion securement assembly and operatively connected to the actuation mechanism and the driven link to transmit a driving force from the actuation mechanism to the driven link to rotate the driven link relative to the first body portion securement assembly; and
a dynamic force mechanism operatively connected to the driven link and the second body portion securement assembly to receive a rotational force from the driven link of the drive assembly, the dynamic force mechanism including a spring and being configured to i) rotate the second body portion securement assembly relative to the first body portion securement assembly using the rotational force until a maximum range of motion of the second body portion securement assembly has been reached, ii) load the spring with dynamic force using the rotational force after the maximum range of motion has been reached, and iii) dynamically impart the dynamic force of the loaded spring upon the second body portion securement assembly after the maximum range of motion has been reached,
wherein the dynamic force mechanism further includes a stop and a connector, wherein the connector operatively connects the spring to the second body portion securement assembly, wherein the stop defines a curved slot having opposite first and second longitudinal ends, wherein the connector includes a shaft extending through the curved slot defined by the stop, wherein the stop is configured to rotate relative to the connector, with the connector within the curved slot, as the spring is loaded with dynamic force such that the second longitudinal end of the curved slot moves toward the connector, wherein the connector is configured to engage the second longitudinal end of the curved slot at a maximum rotation angle of the stop to inhibit further rotation of the driven link to thereby limit loading of the spring of the dynamic force mechanism.

2. An orthosis as set forth in claim 1, wherein the driving link comprises a plurality of driving links.

3. An orthosis as set forth in claim 2, wherein the plurality of driving links comprise a plurality of driving gears.

4. An orthosis as set forth in claim 3, wherein the plurality of driving gears includes a first spur gear and a second spur gear operatively meshed with the first spur gear and the driven link.

5. An orthosis as set forth in claim 4, wherein the driven link comprises a third spur gear.

6. An orthosis as set forth in claim 2, wherein the plurality of driving links includes a bevel ring gear operatively meshed with a bevel pinion gear of the actuation mechanism.

7. An orthosis as set forth in claim 1, wherein the spring is operatively connected to the driven link for rotation therewith.

8. An orthosis as set forth in claim 7, wherein the spring is a clock spring.

9. An orthosis as set forth in claim 1, wherein the first body portion securement assembly comprises a lower leg assembly configured to mount a lower leg of a body and the second body portion securement assembly comprises a foot assembly configured to mount a foot of a body.

10. An orthosis as set forth in claim 9, wherein the foot assembly is configured to rotate relative to the lower leg assembly about an axis of rotation.

11. An orthosis as set forth in claim 10, wherein the foot assembly is configured to move relative to the lower leg assembly in at least one of a plantarflexion and dorsiflexion direction.

12. An orthosis as set forth in claim 1, wherein the stop includes a plate.

* * * * *